United States Patent
Pham et al.

(10) Patent No.: US 6,796,995 B2
(45) Date of Patent: Sep. 28, 2004

(54) INTRAVASCULAR TEMPERATURE CONTROL CATHETER

(75) Inventors: Nora Tran Pham, Lake Forest, CA (US); Hortensia Pompa, San Clemente, CA (US); Peter Barker, Oceanside, CA (US); Lynn Miyeko Shimada, Orange, CA (US)

(73) Assignee: Alsius Corporation, Irvine, CA (US)

( * ) Notice: Subject to any disclaimer, the term of this patent is extended or adjusted under 35 U.S.C. 154(b) by 105 days.

(21) Appl. No.: 10/355,776

(22) Filed: Jan. 31, 2003

(65) Prior Publication Data

US 2004/0044388 A1 Mar. 4, 2004

Related U.S. Application Data

(63) Continuation-in-part of application No. 10/234,084, filed on Aug. 30, 2002, now Pat. No. 6,749,625.

(51) Int. Cl.[7] ................................................... A61F 7/00
(52) U.S. Cl. ...................................... 607/105; 607/106
(58) Field of Search ................................. 607/104–106

(56) References Cited

U.S. PATENT DOCUMENTS 6,261,312 B1 * 7/2001 Dobak et al. ................ 607/105
6,264,679 B1 * 7/2001 Keller et al. ................. 607/105

* cited by examiner

*Primary Examiner*—Roy D. Gibson
(74) *Attorney, Agent, or Firm*—John L. Rogitz

(57) ABSTRACT

An intravascular heat exchange catheter is disclosed that has a non-straight heat exchange element.

19 Claims, 1 Drawing Sheet

INTRAVASCULAR TEMPERATURE CONTROL CATHETER

RELATED APPLICATIONS

This application is a continuation-in-part of U.S. patent application Ser. No. 10/234,084, filed Aug. 30, 2002, now U.S. Pat. No. 6,749,625 for an invention entitled INTRAVASCULAR TEMPERATURE CONTROL CATHETER, incorporated herein by reference and from which priority is claimed.

FIELD OF THE INVENTION

The invention relates to intravascular catheters that can be used to control patient temperature.

BACKGROUND OF THE INVENTION

Intravascular catheters have been introduced for controlling patient temperature. Typically, a coolant such as saline is circulated through an intravascular heat exchange catheter, which is positioned in the patient's bloodstream, to cool or heat the blood as appropriate for the patient's condition. The coolant is warmed or cooled by a computer-controlled heat exchanger that is external to the patient and that is in fluid communication with the catheter.

For example, intravascular heat exchange catheters can be used to combat potentially harmful fever in patients suffering from neurological and cardiac conditions such as stroke, subarachnoid hemorrhage, intracerebral hemorrhage, cardiac arrest, and acute myocardial infarction, or to induce therapeutic hypothermia in such patients. Further, such catheters can be used to rewarm patients after, e.g., cardiac surgery or for other reasons. Intravascular catheters afford advantages over external methods of cooling and warming, including more precise temperature control and more convenience on the part of medical personnel.

The following U.S. patents, all of which are incorporated herein by reference, disclose various intravascular catheters/systems/methods: U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559.

Because it is sometimes desirable that a patient's temperature be changed to a desired value as rapidly as possible, the present invention recognizes the need to provide an intravascular heat exchange that has a relatively large cooling and/or rewarming capacity.

SUMMARY OF THE INVENTION

A heat exchange catheter includes a body, a coolant supply lumen in the body, and a coolant return lumen in the body. A heat exchange element communicates with the lumens and is configured for placement within a blood vessel of a patient such that blood can flow past the heat exchange element. Coolant is circulated through the body in a closed loop. In one embodiment, the heat exchange element includes plural longitudinally-spaced links at least when coolant flows through the catheter, with each link facing its adjacent links and longitudinally overlapping its adjacent links to establish what can be considered an "eagle claw" configuration.

In a preferred non-limiting embodiment the links are longitudinally in sequence with each other. Each preferred link includes a straight hollow top oriented parallel to a long axis of the catheter. Also, each preferred link includes two hollow legs made integrally with the respective top and extending downwardly from opposite ends of the top. The legs may be connected to or made integrally with respective connector segments, with each connector segment connecting a leg of one link with a leg of another link.

At least a portion of each link preferably overlaps respective portions of adjacent links, and is spaced transversely therefrom, such that a longitudinal space is established between every other link.

In another aspect, a heat exchange catheter can include means for conveying coolant. Heat transfer means are connected to the means for conveying coolant. The heat transfer means include non-straight, non-helical link means for exchanging heat with a person's blood.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
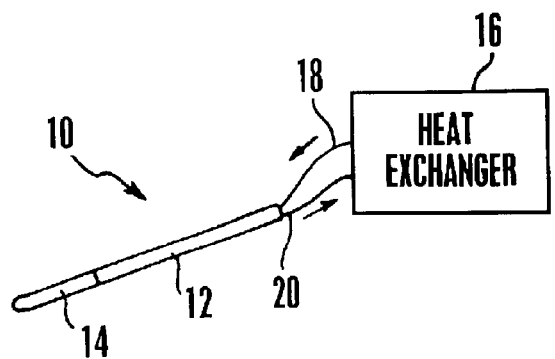
FIG. 1 is a schematic view of the present catheter operably engaged with a heat exchanger system.

Referring initially to FIG. 1, an intravascular heat exchange catheter is shown, generally designated 10, that includes a tubular body 12 and a distal segment 14 that establishes a heat exchange element. Coolant such as but not limited to saline is circulated through the catheter 10 in a closed loop to and from a heat exchanger 16 through coolant supply and return tubes 18, 20 to heat or cool the coolant as desired to warm or cool a patient. The catheter 10 is made of biocompatible material that may be coated with an anti-coagulant substance such as Heperin®. Preferably, the catheter body 12 is made of flexible plastic, with the heat exchange element 14 being made of inflatable and deflatable medical balloon material, although the present heat exchange element principles apply to, e.g., metal structures as well.

In any case, the catheter 10 is sized to fit within the patient's bloodstream without blocking blood flow and without allowing coolant to enter the bloodstream. The blood can flow around substantially all of the exposed surface areas of the heat exchange elements disclosed below when the catheter 10 is positioned in the bloodstream and coolant is being circulated through the catheter, to exchange heat with the blood. In a preferred embodiment, the catheter 10 is configured for placement within the venous system, preferably in the superior vena cava or inferior vena cava through the jugular vein or subclavian vein or femoral vein. Less preferably the catheter 10 may be positioned in the arterial system.

Preferred non-limiting uses for the catheter 10 include inducing mild or moderate therapeutic hypothermia in patients suffering a cardiac arrest, acute myocardial infarction, stroke, brain trauma, or undergoing aneurysm surgery. The catheter 10 may also be used to rewarm such patients as well as rewarm patients post-surgery, e.g., post-cardiac bypass surgery.

Figure 2:
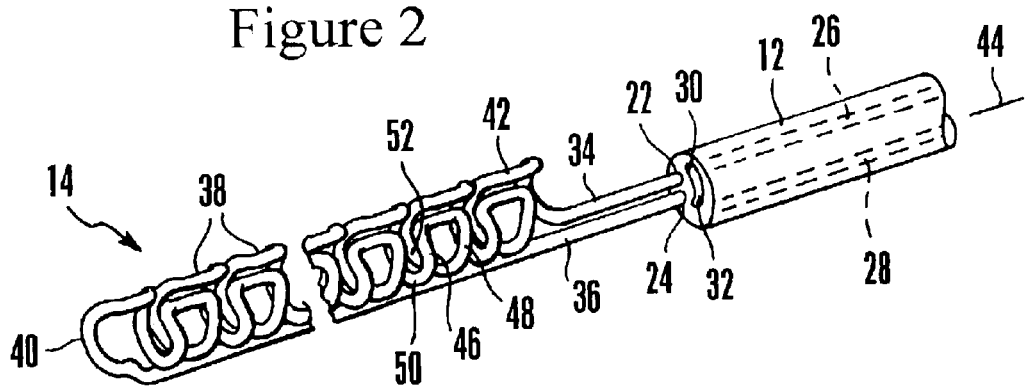
FIG. 2 is a perspective view of the heat exchange element, with portions of the catheter body and heat exchange element broken away with portions broken away.
Figure 3:
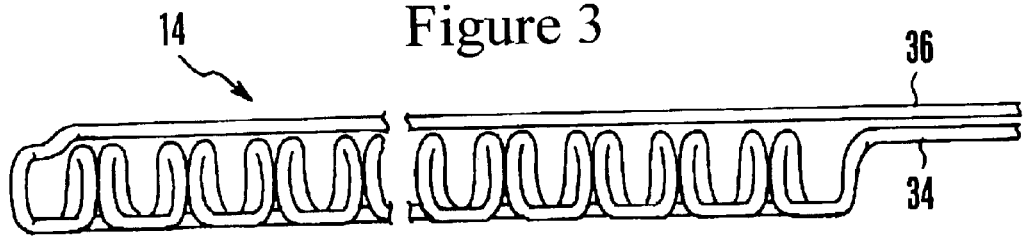
FIG. 3 is a side view of the heat exchange element, with portions broken away for clarity.

Now referring to FIGS. 2 and 3, the preferred catheter body 12 includes a coolant supply lumen 22, a coolant return lumen 24, and one or more (only two shown for clarity) infusion or drug delivery lumens 26, 28 that terminate in respective discharge ports 30, 32 for infusing medicament into a patient's bloodstream or for withdrawing or sampling blood from the patient. While the ports 30, 32 are shown located close together, they may be longitudinally spaced from each other and/or located in the tubular side of the catheter body.

As shown in FIGS. 2 and 3, the preferred heat exchange element 14 includes a coolant supply tube 34 connected to the supply lumen 22 of the catheter body 12, and a coolant return tube 36 connected to the return lumen 24 of the catheter body 12. The supply tube 34 carries coolant to plural longitudinally-spaced links 38 that terminate at a distal end 40 of the heat exchange element 14, with the coolant return tube 36 extending from the distal end 40 to the coolant return lumen 24 in a relatively straight configuration. It is to be understood, however, that the links 38 may also be formed in the coolant return tube, or that links may be formed only in the coolant return tube with the supply tube being straight from its catheter lumen to the distal end of the heat exchange element.

The links 38 assume the shape shown in FIGS. 2 and 3 when coolant flows through the catheter, i.e., when the links are inflated.

In the embodiment shown in FIG. 2, the links are longitudinally in sequence and longitudinally-oriented, i.e., a straight hollow top 42 of each link 38 is oriented parallel to the long axis 44 of the catheter 10. Each link 38 also includes two hollow legs 46, 48 made integrally with the top 42 and extending downwardly from opposite ends of the top 42. The opposite ends of the legs 46, 48 are connected to or made integrally with connector segments 50, 52, with each connector segment 50, 52 connecting a leg of one link 38 with a leg of another link as shown to establish the heat exchange element 14. It is to be understood that terms of relative orientation such as "top", "above", "below" are used for convenience of disclosure, and do not necessarily indicate any orientation regarding catheter placement during heating or cooling. "Distal" and "proximal", however, are with respect to the catheter 10 when it is operationally positioned in the patient.

It can be appreciated in reference to FIGS. 2 and 3 that coolant flows in a generally proximal to distal direction through the links 38. Also, each link 38 faces and longitudinally overlaps its adjacent links. That is, the top 42 of each link 38 somewhat overlaps the tops of the adjacent links, and is spaced transversely therefrom. There is thus a longitudinal space between every other link. The leg/connector segment combination that connects a top 42 to the leg/connector segment combination extending to the top 42 of the adjacent link can be oriented and configured such that it carries coolant in a marginally distal to proximal direction. With this structure, the links are configured to establish an eagle claw configuration.

While the particular INTRAVASCULAR TEMPERATURE CONTROL CATHETER as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for" or, in the case of a method claim, the element is recited as a "step" instead of an "act".

What is claimed is:

1. A heat exchange catheter, comprising:
   a body;
   at least one coolant supply lumen and at least one coolant return lumen in the body; and
   at least one heat exchange element communicating with the lumens and configured for placement within a blood vessel of a patient such that blood can flow past the heat exchange element, wherein coolant is circulated through the body in a closed loop, the heat exchange element including plural longitudinally-spaced links at least when coolant flows through the catheter, each link facing its adjacent links and longitudinally overlapping its adjacent links.

2. The catheter of claim 1, wherein the links are longitudinally in sequence with each other.

3. The catheter of claim 1, wherein each link includes a straight hollow top oriented parallel to a long axis of the catheter.

4. The catheter of claim 3, wherein each link includes two hollow legs made integrally with the respective top and extending downwardly from opposite ends of the top.

5. The catheter of claim 4, wherein the legs are connected to or made integrally with respective connector segments, each connector segment connecting a leg of one link with a leg of another link.

6. The catheter of claim 1, wherein at least a portion of each link overlaps respective portions of adjacent links, and is spaced transversely therefrom, a longitudinal space being established between every other link.

7. The catheter of claim 5, wherein a leg/connector segment combination that connects a top of a link to a leg/connector segment combination extending to a top of an adjacent link is oriented and configured such that coolant flows in a distal to proximal direction through at least one leg/connector segment combination.

8. The catheter of claim 1, wherein the body is formed with at least one drug delivery lumen.

9. The catheter of claim 8, wherein the body has two drug delivery lumens.

10. A heat exchange catheter, comprising:

a body;

at least one coolant supply lumen and at least one coolant return lumen in the body; and at least one heat exchange element communicating with the lumens and configured for placement within a blood vessel of a patient such that blood can flow past the heat exchange element, wherein coolant is circulated through the body in a closed loop, the heat exchange element including plural longitudinally-spaced links at least when coolant flows through the catheter, the links being configured to establish an eagle claw configuration.

11. The catheter of claim 10, wherein each link faces its adjacent links and longitudinally overlapping its adjacent links.

12. The catheter of claim 10, wherein the links are longitudinally in sequence with each other.

13. The catheter of claim 10, wherein each link includes a straight hollow top oriented parallel to a long axis of the catheter.

14. The catheter of claim 13, wherein each link includes two hollow legs made integrally with the respective top and extending downwardly from opposite ends of the top.

15. The catheter of claim 14, wherein the legs are connected to or made integrally with respective connector segments, each connector segment connecting a leg of one link with a leg of another link.

16. The catheter of claim 10, wherein at least a portion of each link overlaps respective portions of adjacent links, and is spaced transversely therefrom, a longitudinal space being established between every other link.

17. The catheter of claim 15, wherein a leg/connector segment combination that connects a top of a link to a leg/connector segment combination extending to a top of an adjacent link is oriented and configured such that coolant flows in a distal to proximal direction through at least one leg/connector segment combination.

18. The catheter of claim 10, wherein the body is formed with at least one drug delivery lumen.

19. The catheter of claim 18, wherein the body has two drug delivery lumens.

* * * * *